(12) United States Patent
Wietelmann et al.

(10) Patent No.: US 9,163,097 B2
(45) Date of Patent: Oct. 20, 2015

(54) LOW-VISCOSITY, CONCENTRATED SOLUTIONS OF MAGNESIUM COMPLEXES FOR PRODUCING POLYMERIZATION CATALYSTS AND METHOD FOR PRODUCING THE SAME

(75) Inventors: Ulrich Wietelmann, Friedrichsdorf (DE); Jens Röder, Mannheim (DE); Ute Emmel, Frankfurt am Main (DE)

(73) Assignee: Chemetall GmbH, Frankfurt am Main (DE)

( * ) Notice: Subject to any disclaimer, the term of this patent is extended or adjusted under 35 U.S.C. 154(b) by 133 days.

(21) Appl. No.: 13/876,644

(22) PCT Filed: Sep. 29, 2011

(86) PCT No.: PCT/EP2011/066981
§ 371 (c)(1),
(2), (4) Date: Jul. 8, 2013

(87) PCT Pub. No.: WO2012/041960
PCT Pub. Date: Apr. 5, 2012

(65) Prior Publication Data
US 2013/0296161 A1    Nov. 7, 2013

(30) Foreign Application Priority Data
Sep. 30, 2010  (DE) .......................... 10 2010 046 978

(51) Int. Cl.
| | | |
|---|---|---|
| *C08F 4/50* | (2006.01) |
| *C08F 10/00* | (2006.01) |
| *C08F 4/655* | (2006.01) |
| *B01J 31/02* | (2006.01) |
| *C07C 69/80* | (2006.01) |
| *C07C 69/96* | (2006.01) |
| *C07F 3/00* | (2006.01) |
| *C08F 4/651* | (2006.01) |
| *C08F 4/654* | (2006.01) |

(52) U.S. Cl.
CPC . *C08F 4/50* (2013.01); *C07F 3/003* (2013.01); *C08F 4/651* (2013.01); *C08F 4/6548* (2013.01)

(58) Field of Classification Search
None
See application file for complete search history.

(56) References Cited

U.S. PATENT DOCUMENTS

| | | | |
|---|---|---|---|
| 6,653,254 B1 | 11/2003 | Shamshoum et al. |
| 2010/0056359 A1 | 3/2010 | Denifl et al. |

FOREIGN PATENT DOCUMENTS

| | | | |
|---|---|---|---|
| EP | 1 031 580 A1 | 8/2000 |
| EP | 1 229 054 A1 | 8/2002 |
| EP | 1 862 480 A1 | 12/2007 |
| WO | 85/02176 A1 | 5/1985 |

OTHER PUBLICATIONS

Butyloctylmagnesium—A 20% in Heptane, technical data sheet published by Chemura Corporation Oct. 2013.
Phthaloyl dichloride, CAS No. 88-95-9, printed out on Apr. 17, 2015 from www.chemicalbook.com/ChemicalProductProperty_EN_CB7273160.htm.

*Primary Examiner* — Yun Qian
(74) *Attorney, Agent, or Firm* — Norton Rose Fulbright US LLP

(57) ABSTRACT

This invention relates to low-viscosity, concentrated complex solutions containing magnesium, which are produced by reacting a magnesium alkoside with a carboxylic acid halogenide in a hydrocarbon-based solvent, and to a method for producing the same.

17 Claims, 1 Drawing Sheet

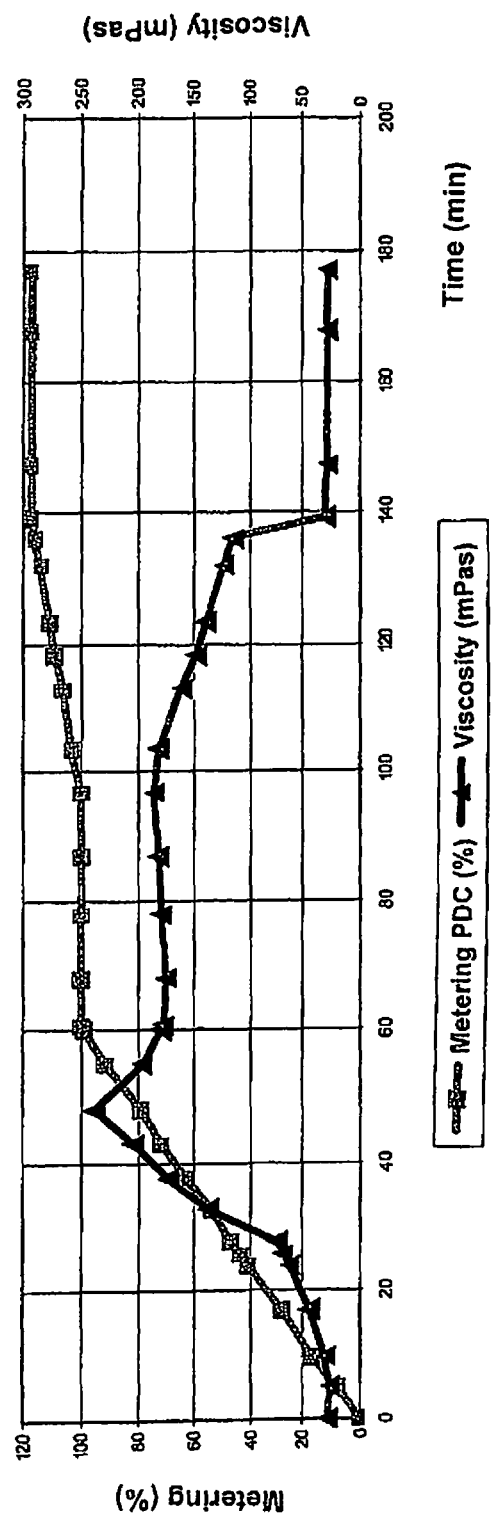

LOW-VISCOSITY, CONCENTRATED SOLUTIONS OF MAGNESIUM COMPLEXES FOR PRODUCING POLYMERIZATION CATALYSTS AND METHOD FOR PRODUCING THE SAME

This application is a §371 of International Application No. PCT/EP2011/066981 filed Sep. 29, 2011, and claims priority from German Patent Application No. 10 2010 046 978.5 filed Sep. 30, 2010.

The invention relates to concentrated, low-viscosity solutions of basic magnesium complexes in hydrocarbon-based solvents, and a method for producing the same.

Magnesium alkoxides are used, inter alia, in the production of supported olefin polymerization catalysts of the Ziegler-Natta type. Used for this purpose are, for example, insoluble alkoxides such as, for example, magnesium ethoxide in form of spherical particles that are converted into the active form by reacting the some with titanium chloride or another compound that includes titanium halogen bonds, such as dicyclopentadienyl titanium dichloride ($Cp_2TiCl_2$), as described in document EP 1031580:

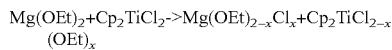

$Mg(OEt)_2 + Cp_2TiCl_2 \rightarrow Mg(OEt)_{2-x}Cl_x + Cp_2TiCl_{2-x}(OEt)_x$ (x=0 to 2)

A further possibility of producing supported Ziegler-Natta catalysts provides for starting from soluble magnesium alkoxides. While most magnesium alcoholates, such as, for example, magnesium salts of methanol, ethanol, propanol, isopropanol, tert-butanol, etc., are insoluble in aprotic solvents, magnesium compounds of primary alcohols having a branching in position 2 show themselves as soluble in hydrocarbons (WO 85/02176). Therefore, for example, magnesium salts of 2-methyl-1-pentanol or of 2-ethyl-1-hexanol should dissolve in concentrations of 1,3 mol/l in cyclohexane. Mixed magnesium alkoxides as well, meaning those having two different alkoxide moieties $Mg(OR^1)(OR^2)$ can be soluble in hydrocarbon when the corresponding alcohol $R^1OH$ is a primary alcohol that is branched in position 2, and the corresponding alcohol $R^2OH$ is a secondary alcohol (WO 85/02176).

From solutions containing such magnesium alcoholates, it is possible to prepare, in a first step for the production of the $MgCl_2$-based catalyst support, a soluble complex compound by reacting the same with carboxylic acid halogenides. Preferred carboxylic acid halogenides are dicarboxylic acid dihalogenides, particularly preferred are α,β-unsaturated dicarboxylic acid halogenides, especially phthaloyl chloride (EP 1229054B1). The production of such a preferred complex solution, the synthesis of which uses, aside from a carboxylic acid halogenide, no further halogen-containing compound, has been described in EP 1862480A1. Accordingly, first a 20% butyloctyl magnesium solution is reacted in toluene with 2 equivalents (eq.) ethylhexanol to obtain soluble magnesium bis(ethylhexoxide) that is subsequently reacted with phthaloyl dichloride at 60° C. At 100% yield, the product solution contains a magnesium concentration of 0.83 mmol/g, and used the molar ratio of phthaloyl chloride relative to magnesium bis(ethylhexoxide) is 0.40 to 1.

Disadvantageously, the product concentration of this product is quite minimal, and the product solutions have high viscosity at concentrations>0.9 mmol/g magnesium concentration.

It is the object of the present invention to describe a product that avoids the disadvantages of the prior art, meaning that it contains a concentration of at least 0.9 mmol/g magnesium in dissolved form;
has low viscosity (viscosity<500 mPas); and
has a shelf life of up to four weeks at temperatures of up to 30° C.

The object is achieved in that solutions containing magnesium alcoholate are reacted with one or a plurality of carboxylic acid halogenides in a hydrocarbon-based solvent or solvent mixture, wherein the dissolved magnesium concentration in the complex that is formed in this manner is at least 0.9 mmol/g, particularly preferred 1 mmol/g and particularly preferred 1.1 mmol/g. The molar ratio between the carboxylic acid halogenide function and magnesium is at least 0.84:1, particularly preferred at least 0.9:1 and at a maximum 1.8:1. Particularly preferred as carboxylic acid halogenides is the use of dicarboxylic acid dichlorides, such as, for example, phthaloyl dichloride. With bifunctional acid chlorides of this kind, the molar ratio of dicarboxylic acid dichloride relative to magnesium alcoholate is at least 0.42:1, preferably at least 0.45:1, particularly preferred at least 0.50:1 and at most 0.9:1. Surprisingly, it was found that when a molar ratio of approximately 0.9:1 carboxylic acid chloride equivalents relative to magnesium alcoholate equivalents was exceeded, a dramatic viscosity reduction of the solvent occurs. This unanticipated effect has the consequence that the product concentration of the complex can be considerably increased between the magnesium alcoholate and the carboxylic acid halogenide without the viscosity increasing such that handling of the product is rendered more difficult. In particular, such product solutions according to the invention having low viscosity can be very easily pumped and demonstrate a good shelf life.

Used as magnesium alcoholates are compounds of the general formula $Mg(OCH_2R^1)_2$ that are derived from primary alcohols ($HOCH_2R^1$) branching off in the 2-position. It is particularly preferred to select the alcohol $HOCH_2R^1$ from the group consisting of: isobutanol, 2-methyl-1-pentanol, 2-ethyl-1-butanol, 2-ethyl-1-pentanol, 2-ethyl-4-methyl-1-pentanol, 2-propyl-1-heptanol, 2-methyl-1-hexanol, 2-ethylhexanol and 2-ethyl-5-methyl-1-octanol, or any type of mixture of at least two of the listed alcohols.

The hydrocarbon-based solvent is or contains at least one or a plurality of aliphatic compounds having 5 to 20 C-atoms, wherein cyclical as well as open-chained compounds are possible. Preferred are: cyclohexane, methyl cyclohexane, hexane, heptane, octane, nonane, decane, dodecane, decahydronaphthalene, as well as any commercially available boiling fractions (gasoline fractions).

It is further possible for the aprotic solvent to contain or be made of aromatics. Preferred are: benzene, toluene, ethylbenzene, xylene as well as cumene.

In a further embodied example of the invention, the magnesium-containing complex solution according to the invention can also contain polar, aprotic solvents, such as, for example, ether or tertiary amines.

The concentrated reaction products according to the invention from magnesium alcoholates and carboxylic acid chlorides generally have a maximum dynamic solution viscosity of 500 mPas at room temperature, preferably a maximum of 100 mPas and especially preferred of a maximum of 50 mPas, measured by rotational viscosimeter (for example, by the company Brookfield).

The preparation of the complex solution according to the invention occurs by reacting the solution of a magnesium acoholate that is branched in position 2, for example magnesium-bis(ethylhexoxide), with a carboxylic acid halogenide in a hydrocarbon-based solvent at temperatures between 0° C.

and 120° C., preferably 20° C. and 100° C. The reaction vessel and the used feed materials must be dry and free of air, meaning they must have been rendered inert. The reaction occurs in a protective gas atmosphere, for example under nitrogen or argon. Preferably, the alcoholate solution is filled into a vessel with the carboxylic acid halogenide metered thereto. To be able to monitor changes in viscosity, an in-line viscosity measurement is taken. An instrument for this purpose can be obtained, for example, from the company F5, Wunstorf, Lower Saxony, Germany.

Filled in a container was a low-viscosity 33.7% magnesium-bis(ethylhexoxide) solution (1.19 mmol/g magnesium, viscosity approximately 11 mPas) in a solvent mixture of 90% toluene and 10% heptane, then heated to 60° C. To this were added first 0.40 eq. phthaloyl dichloride (corresponding to a dosage=100%). This caused a very strong increase of viscosity to approximately 180 mPas, measured with the instrument by the company F5. Said viscosity corresponds to a dynamic viscosity of several 1000 mPas, measured by rotational viscosimeter (for example, by the company Brookfield). After stirring for approximately 40 minutes at 60° C., more phthaloyl dichlorid ("PDC") was added. After adding further 0.07 eq. PDC for a total of 0.47 eq., the viscosity, as measured with the instrument by the company F5, dropped virtually all of a sudden from approximately 115 to 20 mPas.

The products according to the invention are used in the preparation of polymerization catalysts, particularly heterogenized polyolefin catalysts of the Ziegler-Natte type.

FIG. 1 shows the typical course of viscosity during such a conversion.

The invention will be described in further detail based on the following two examples and two comparison examples:

EXAMPLES

All reactions were done in dry glass instruments rendered inert with argon. Viscosity measurements were taken at room temperature, using a rotational viscosimeter by the company Brookfield, in an argon-filled glove box.

Comparison Example 1

544 g magnesium bis(ethylhexoxide) solution in toluene having a magnesium concentration of 1.23 mmol/g (ICP analysis) and a viscosity of 560 mPas was filled into a 0.5 L double-Jacket reactor with an agitation element close to the walls and heated to 60° C. 54.3 g (corresponding to 0.40 eq. relative to the filled-in quantity of magnesium alcoholate) was then dropped in over the course of 1 hour. This caused the solution to become very viscous. After stirring for 20 minutes at 60° C., the solution was cooled to room temperature.

Weigh-in: 583 g solution
Mg concentration: 1.12 mmol/g
Viscosity: 3200 mPas

Comparison Solution 2

532 g magnesium bis(ethylhexoxide) solution in a solvent mixture of 70% toluene and 30% heptane having a concentration of 1.24 mmol/g (ICP analysis) and a viscosity of 500 mPas was filled into a 0.5 L double-jacket reactor with an agitation element close to the wails and heated to 60° C. 53.5 g (corresponding to 0.40 eq. relative to the filled-in quantity of magnesium alcoholate) was then dropped in over the course of 1 hour. This caused the solution to become extremely viscous.

After stirring for 20 minutes at 60° C., the solution was cooled to room temperature.

Weigh-in: 552 g solution
Mg concentration: 1.15 mmol/g
Viscosity: 6200 mPas

Example 1

432 g magnesium bis(ethylhexoxide) solution in a solvent mixture of 70% toluene and 30% heptane having a magnesium concentration of 1.24 mmol/g (ICP analysis) and a viscosity of 500 mPas was filled into the instrumentation as described in Comparison Example 1 and heated to 60° C. 57.6 g PDC (corresponding to 0.53 eq. relative to the filled-in quantity of magnesium alcoholate) was then dropped in over the course of 1 hour. Until the metering of approximately 0.5 eq., the solution became visibly more viscous, but with shortly before the end of metering viscosity dropping considerably. After stirring for 20 minutes at 60° C., the solution was cooled to room temperature.

Weigh-in: 462 g solution
Mg concentration: 1.15 mmol/g
Viscosity: 18 mPas
Shelf life: no changes over 4 weeks at temperatures of 0° C., 10° C. and approximately 26° C.

Example 2

432 g magnesium bis(ethylhexoxlde) solution in a solvent mixture of 90% toluene and 10% heptane having a magnesium concentration of 1.49 mmol/g (ICP analysis) and a viscosity of 1500 mPas was filled into the instrumentation as described in Comparison Example 1 and heated to 60° C. 61.5 g PDC (corresponding to 0.47 eq. relative to the filled-in quantity of magnesium alcoholate) was then dropped in over the course of 1 hour. Until the metering of approximately 0.4 eq, the solution became visibly more viscous, but with shortly before the end of metering viscosity dropping considerably. After stirring for 20 minutes at 60° C., the solution was cooled to room temperature.

Weigh-in: 415 g solution
Mg concentration: 1.31 mmol/g
Viscosity: 30 mPas
Shelf life: no changes over 4 weeks at temperatures of 0° C., 10° C. and approximately 25° C.

Comparison example 1 shows that a concentrated magnesium complex solution in pure toluene has, with use of PDC of 0.40 eq. per mol magnesium alcoholate, a very high viscosity of 3200 mPas. If, instead of toluene, a mixture of 70% toluene and 30% heptene is selected, using the same PDC feed of 0.40 eq., a still higher viscosity of 6200 mPas was observed (Comparison Example 2).

In contrast, using an identical magnesium alcoholate solution as in Comparison Example 2, but with increase of the PDC stoichiometry to 0.53, eq. there results a highly fluid magnesium complex solution (18 mPas, Example 1). Example 2 shows that even a still higher magnesium complex concentration of 1.31 mmol/g has a low viscosity if 0.47 eq. PDC per eq. of used magnesium alkoxide are employed.

The invention claimed is:
1. A solution comprising a reaction product of a magnesium alkoxide of formula $Mg(OCH_2R^1)_2$ with a carboxylic acid halogenide in a hydrocarbon solvent, wherein a dissolved magnesium concentration is at least 0.9 mmol/g and a molar ratio between the carboxylic acid halogenide and the magnesium alkoxide is at least 0.84:1, wherein the $OCH_2R^1$ group of the magnesium alkoxide is branched in a 2-position thereof.

2. The solution of claim 1, wherein the dissolved magnesium concentration is at least 1 mmol/g.

3. The solution of claim 1, wherein the dissolved magnesium concentration is at least 1.1 mmol/g.

4. The solution of claim 1, wherein the molar ratio between carboxylic acid halogenide functions and magnesium is at least 0.9:1.

5. The solution of claim 1, wherein the molar ratio between carboxylic acid halogenide functions and magnesium is at most 1.8:1.

6. The solution of claim 1, wherein, at room temperature, the solution has a dynamic solution viscosity of a maximum of 500 mPas when measured by rotational viscosimeter.

7. The solution of claim 1, wherein the carboxylic acid halogenide is a dicarboxylic acid dichloride.

8. The solution of claim 1, wherein the carboxylic acid halogenide is phthaloyl dichloride.

9. The solution of claim 1, wherein the hydrocarbon solvent comprises at least one member selected from the group consisting of an aliphatic compound having 5 to 20 C-atoms, wherein the aliphatic compound is open chained or cyclical.

10. The solution of claim 1, wherein the hydrocarbon solvent comprises at least one member selected from the group consisting of cyclohexane, methyl cyclohexane, hexane, heptane, octane, nonane, decane, dodacane and decahydronaphthalene.

11. The solution of claim 1, wherein the hydrocarbon solvent comprises an aromatic compound.

12. The solution of claim 11, wherein the aromatic compound is selected from the group consisting of benzene, toluene, ethylbenzene, xylene and cumene.

13. The solutions according to claim 1, wherein the solution further comprises a polar, aprotic solvent.

14. The solution according to claim 1, wherein the solution further comprises an ether or a tertiary amine.

15. A solution comprising a reaction product of a magnesium alkoxide with a carboxylic acid halogenide in a hydrocarbon solvent, wherein a dissolved magnesium concentration is at least 0.9 mmol/g and a molar ratio between the carboxylic acid halogenide and the magnesium alkoxide is at least 0.84:1, wherein the alcohol is selected from the group consisting of isobutanol, 2-methyl-1-pentanol, 2-ethyl-1-butanol, 2-ethyl-1-pentanol, 2-ethyl-4-methyl-1-pentanol, 2-propyl-1-heptanol, 2-methyi-1-hexanol, 2-ethylhexanol and 2-ethyl-5-methyl-l-octanol.

16. A method for preparing magnesium-containing complex solution according to claim 1 comprising reacting the carboxylic acid halogenide with the magnesium alkoxide in the hydrocarbon solvent at a molar ratio of at least 0.84:1 to 1.8:1.

17. The method according to claim 16, wherein the reaction occurs at a temperature between 0° C. and 120° C.

* * * * *